(12) United States Patent
Ben-Natan et al.

(10) Patent No.: US 10,758,429 B2
(45) Date of Patent: Sep. 1, 2020

(54) ANTI-IRRITANT DIAPER

(71) Applicants: Chaim Ben-Natan, Kfar Chabad (IL); Amichai Ben-Natan, Tzfat (IL)

(72) Inventors: Chaim Ben-Natan, Kfar Chabad (IL); Amichai Ben-Natan, Tzfat (IL)

(*) Notice: Subject to any disclaimer, the term of this patent is extended or adjusted under 35 U.S.C. 154(b) by 345 days.

(21) Appl. No.: 15/949,094

(22) Filed: Apr. 10, 2018

(65) Prior Publication Data
US 2018/0228663 A1 Aug. 16, 2018

Related U.S. Application Data

(63) Continuation of application No. 14/413,010, filed on Jan. 6, 2015, now abandoned.

(51) Int. Cl.
| | | |
|---|---|---|
| *A61F 13/495* | (2006.01) | |
| *A61F 13/505* | (2006.01) | |
| *A61F 13/494* | (2006.01) | |
| *A61F 13/66* | (2006.01) | |
| *A61F 13/15* | (2006.01) | |
| *A61F 13/56* | (2006.01) | |
| *A61F 13/62* | (2006.01) | |

(52) U.S. Cl.
CPC ...... *A61F 13/495* (2013.01); *A61F 13/15268* (2013.01); *A61F 13/49413* (2013.01); *A61F 13/505* (2013.01); *A61F 13/5633* (2013.01); *A61F 13/62* (2013.01); *A61F 13/66* (2013.01); *A61F 2013/15276* (2013.01); *A61F 2013/4955* (2013.01); *A61F 2013/4956* (2013.01); *F04C 2270/041* (2013.01)

(58) Field of Classification Search
CPC .............. A61F 13/49003; A61F 13/493; A61F 13/49413; A61F 13/495; A61F 13/505; A61F 2013/4951; A61F 2013/4953; A61F 2013/4955; A61F 2013/4956; A61F 2013/4958
See application file for complete search history.

(56) References Cited

U.S. PATENT DOCUMENTS

| | | | | |
|---|---|---|---|---|
| 5,573,524 A | * | 11/1996 | Sardo ................ | A61F 13/493 604/358 |
| 5,618,279 A | * | 4/1997 | Pudlo ................ | A61F 5/40 2/403 |

(Continued)

*Primary Examiner* — Catharine L Anderson
(74) *Attorney, Agent, or Firm* — Mark M. Friedman

(57) ABSTRACT

There is provided an anti-irritant diaper having an absorbent material constructed with a shape defined by a front area, a middle area, a rear area, a pair of leg cuffs and closing tabs. A resilient, flexible band is removably disposed longitudinally and centrally along the absorbent material. A pocket is formed within the middle area for receiving excreted solid waste, so that the pocket forms a space above it separating the pocket from the wearer's skin, the flexible band maintains the structure of the pocket. There is also provided a removable one-directional flexible partition having a pair of dividers situated above the pocket, each of the dividers being attached at one end to one of the pair of leg cuffs, each divider being segmented into a plurality of flaps. The flexible band maintains the structure of the pocket, such that the partition allows for solid waste to enter therethrough and into the pocket and prevents the waste from returning and then contacting the skin, thereby preventing irritation to the skin.

14 Claims, 7 Drawing Sheets

(56) References Cited

U.S. PATENT DOCUMENTS

| | | | | |
|---|---|---|---|---|
| 5,817,086 A * | 10/1998 | Kling | ............... | A61F 13/495 |
| | | | | 604/385.19 |
| 6,464,678 B2 * | 10/2002 | Shimoe | ............ | A61F 13/49019 |
| | | | | 604/385.04 |
| 7,842,019 B2 * | 11/2010 | Sugiyama | ......... | A61F 13/49473 |
| | | | | 604/385.01 |
| 8,870,840 B2 * | 10/2014 | Close | ............... | A61F 13/471 |
| | | | | 604/385.09 |
| 9,375,364 B2 * | 6/2016 | Suzuki | ............ | A61F 13/49017 |
| 9,883,977 B1 * | 2/2018 | Cooper | ............... | A61F 13/505 |

\* cited by examiner

ANTI-IRRITANT DIAPER

CROSS-REFERENCE TO RELATED APPLICATIONS

The present invention is a Continuation-In-Part of US National Stage patent application Ser. No. 14/413,010 which claims the priority date of US Provisional Patent Application No. 61/670,608 filed on 12 Jul. 2012, by one of the co-applicants herein.

FIELD OF THE INVENTION

The present invention relates to diapers, in particular to diapers constructed for protection from skin irritation.

BACKGROUND OF THE INVENTION

Use of disposable diapers has provided a convenient and sanitary solution for parents of infants and care-givers to the elderly. However, there are some disadvantages as well. First of all, disposable diapers contain chemicals which can irritate a baby's skin, causing diaper rash and worse.

Secondly, approximately 90-95% of American babies use 27.4 billion single-use, plastic diapers every year. This generates 7.6 billion pounds of garbage each year. It is estimated to require between 250 and 500 years for a single disposable diaper to break down in a landfill.

And lastly, disposable diapers are expensive, estimated to cost approximately $2000 per child in 2.5 years.

The solution for these problems is using cloth diapers instead. Cloth diapers are used over and over before heading to the landfill, and they require about 5 months to break down. They are less costly and although they cost more upfront, they save costs considerably in the long run.

However, diaper rash caused by the contact of bodily waste with the skin is still a problem for disposable and cloth diapers alike. It would be beneficial to come up with a solution for this problem which is inflicted upon babies and adults wearing diapers.

The contact between solid or semi-solid waste (hereinafter "solid waste") waste and the skin can cause irritation and even pain, especially if the diaper-wearer has sensitivity to certain types of food. Also, care-givers suffer from discomfort and repulsion caused by changing soiled diapers and having to scrub the waste off the patient's skin with soap and water. In addition, solid waste often leakes from the diaper onto the legs and clothes.

A solution for the above-mentioned problems has been proposed by the applicant in U.S. Pat. No. 6,464,673 and U.S. patent application Ser. No. 14/413,010, both disclosing a diaper having a solid waste containment means. The present invention is an improvement of the above-mentioned inventions.

SUMMARY OF THE INVENTION

The present invention overcomes the problems associated with the prior art by providing an anti-irritant diaper construction which contains solid waste and distances the surface of the absorbent material from the skin of the user.

In a preferred embodiment of the present invention there is provided an anti-irritant diaper having an interior, a front area, a middle area, a rear area, leg cuffs and closing means, comprising:

an absorbent material constructed with a shape defined by a front area, a middle area, a rear area, a pair of leg cuffs and closing tabs;

a resilient, flexible band removably disposed longitudinally and centrally along said absorbent material;

a pocket formed within said middle area for receiving excreted solid waste, said pocket forming a space above it separating said pocket from the wearer's skin, said flexible band maintaining the structure of said pocket; and a removable transverse flexible partition comprising a pair of dividers, having two transverse ends, situated above said pocket, each attached on one end to one of said pair of leg cuffs, each said divider being segmented into a plurality of flaps, one directional wherein said flexible band maintains the structure of said pocket, such that said flexible partition allows for solid waste to enter therethrough and into said pocket and prevents the waste from returning and then contacting the skin, thereby preventing irritation to the skin.

According to the preferred embodiment of the present invention there is provided a diaper having a resilient flexible band disposed longitudinally and centrally along it which defines a pocket having a depth, in the middle of the diaper. The pocket contains solid waste excreted from the wearer, and maintains it within. The pocket forms a space between the diaper and the wearer's skin so as to prevent the waste from coming in contact with the skin of the wearer, so as not to cause rashes. This also makes cleaning the diaper-wearer easier, during the diaper changing process, since the skin remains relatively clean. The flexible band may be bent by the movement of the wearer, for example when sitting down, and because the band is resilient, it returns to its original shape once the diaper-wearer returns to an upright position.

According to another preferred embodiment of the present invention, the diaper may be disposable or may be made of cloth for multiple use.

The embodiment of the disposable diaper also helps reduce the amount of waste, because the diaper can be changed less frequently than regular known diapers.

According to yet another preferred embodiment of the present invention, the flexible band may be removed from the diaper and re-inserted into a new one.

The present invention is useful for both infants and the elderly who cannot control their bowel movements. The diaper allows the diaper-wearer to be more mobile, since the solid waste is contained inside the pocket of the diaper and so, does not allow it to escape onto the legs and clothes, as often occurs when using a regular diaper. The contact between the waste and the skin is reduced to a minimum, if any, so that any feeling of discomfort is decreased. It is especially useful in places and situations where it is difficult to change the diaper, and the wearer is forced to remain with the soiled diaper for an extended period of time which by then, typically, would cause irritation to the skin.

The present invention is also especially useful for elderly patients in a nursing home, who are treated by care-givers whom also change their diapers. The process of changing diapers causes repulsion and disgust on behalf of the changer. The inventive diaper will minimize the care-giver's exposure to the solid waste during changing, because the waste will be safely contained inside the dedicated pocket.

The inventive diaper may also reduce the number of staff needed to care for the patients, since a great deal of time and work put into cleaning the patients, can be saved.

In yet another embodiment of the present invention there is provided a flexible band that is attached to the diaper but is inserted internally to the diaper, via a designated sleeve so it is not visible. The designated sleeve maintains the flexible band in its position, thereby maintaining the shape of the pocket.

In an additional embodiment of the present invention there is provided an external sleeve, designated for the insertion of the resilient flexible band.

In another additional embodiment of the present invention there is provided a resilient flexible band disposed transversely to the diaper, stretching from the right cuff to the left cuff.

In yet another preferred embodiment of the present invention there is provided a removable transverse one-directional flexible partition, situated above the pocket. The solid waste passes through the partition and into the pocket, and then it provides a cover over the waste to that the waste does not touch the skin. The flexible partition is made of a pair of dividers which are segmented into a plurality of flaps for preventing from the dividers to resist the weight of the waste. After the waste passes through the dividers, due to their flexibility, they return to their original position so that they function as a cover over the waste and therefore serve as a partition between the waste and the skin.

The removable transverse one-directional flexible partition may be disposable for one use only, or may be washed for multiple use.

In yet another embodiment of the present invention there is provided a cover for the pocket area, which can be pulled over the pocket by pulling a string external to the diaper, so that the solid waste captured in the pocket will not touch the skin. The cover may be spread by pulling the string on the opposite side to expose the pocket in the case of re-use by the diaper wearer. This feature is especially suitable for the elderly, who can spread and fold the cover themselves, more than once if needed, taking into consideration the diaper's capacity limit.

Additional features and advantages will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout and in which.

DETAILED DESCRIPTION OF THE EMBODIMENTS

Figure 1:
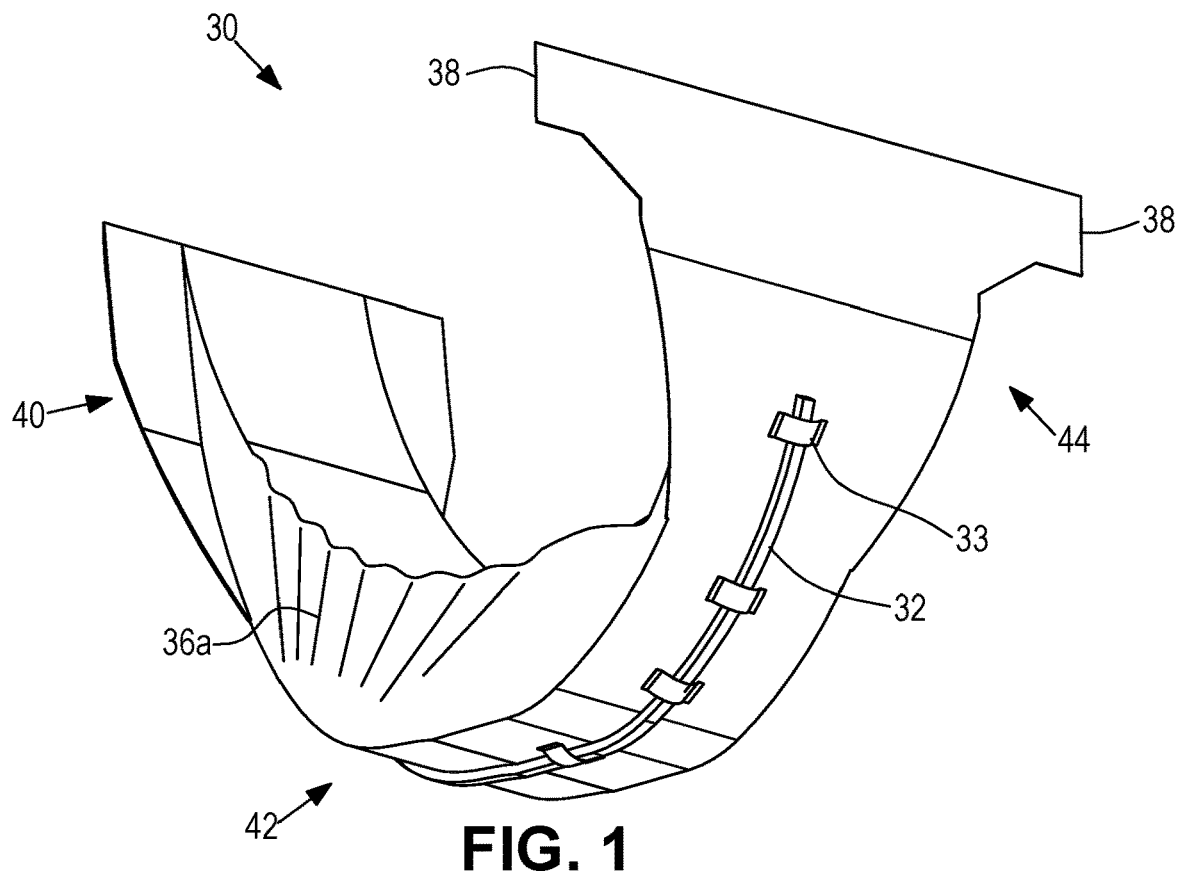
FIG. 1 shows a back bottom perspective view of the diaper of the preferred embodiment of the present invention having a flexible band disposed externally to the diaper.

Referring now to FIG. 1, there is shown diaper 30 constructed in accordance with the principles of the present invention. Diaper 30 is constructed of a front area 40, a middle area 42 and a rear area 44. The rear area 44 has two fasteners 38, one on each side (as in conventional diapers) for closing the diaper. Middle area 42 comprises side cuffs 36a, 36b, one on each side (as in conventional diapers).

A resilient, flexible band 32 is removably disposed longitudinally and centrally along the outer side of diaper 30, from front area 40, continuing onto middle area 42 to rear area 44. Flexible band 32 is attached to diaper 30 by stick-on tabs 33. Flexible band 32 defines a pocket 34 (shown in FIG. 3) formed in middle area 42, and maintains its shape. Solid waste released from the wearer of diaper 30 falls into pocket 34 and is maintained there, thereby being prevented from leaking out of diaper 30. Pocket 34 is important for creating a gap between the waste and the user's skin to avoid irritation. Flexible band 32 is fabricated from a material that is rigid enough to maintain the form of pocket 34 while being resilient so that in the event the wearer sits down and thereby causes band 32 to bend, the band 32 will return to its original shape once the wearer stands in an upright position, thereby maintaining the shape of pocket 34. The waste stored in pocket 34 is safely kept away from the skin, thereby preventing irritation.

In the event of diaper 30 becoming full of urine so that it becomes heavy, flexible band 32 retains diaper 30 close to the wearer's body and does not allow diaper 30 to hang low between the legs.

Flexible band 32 may be removed from diaper 30 and placed on another diaper 32, so that there is a need for only one band 32 which can be re-used for multiple diaper 30 uses. Diaper 30 may be a multiple-use cloth diaper or a disposable type. A multi-use diaper 30 helps reduce the amount of waste caused by the wide usage of disposable diapers. Disposable diaper 30 also helps reduce the amount of waste, because the diaper 30 can be changed less frequently than regular known diapers.

The size of diaper 30 may be adapted to fit various sizes of wearers, from new-born babies to the elderly, and so the dimensions of the flexible band 32 are varied to fit these different-sized diapers 30, in order to form a suitable pocket 34 in the middle area 42.

Figure 2:
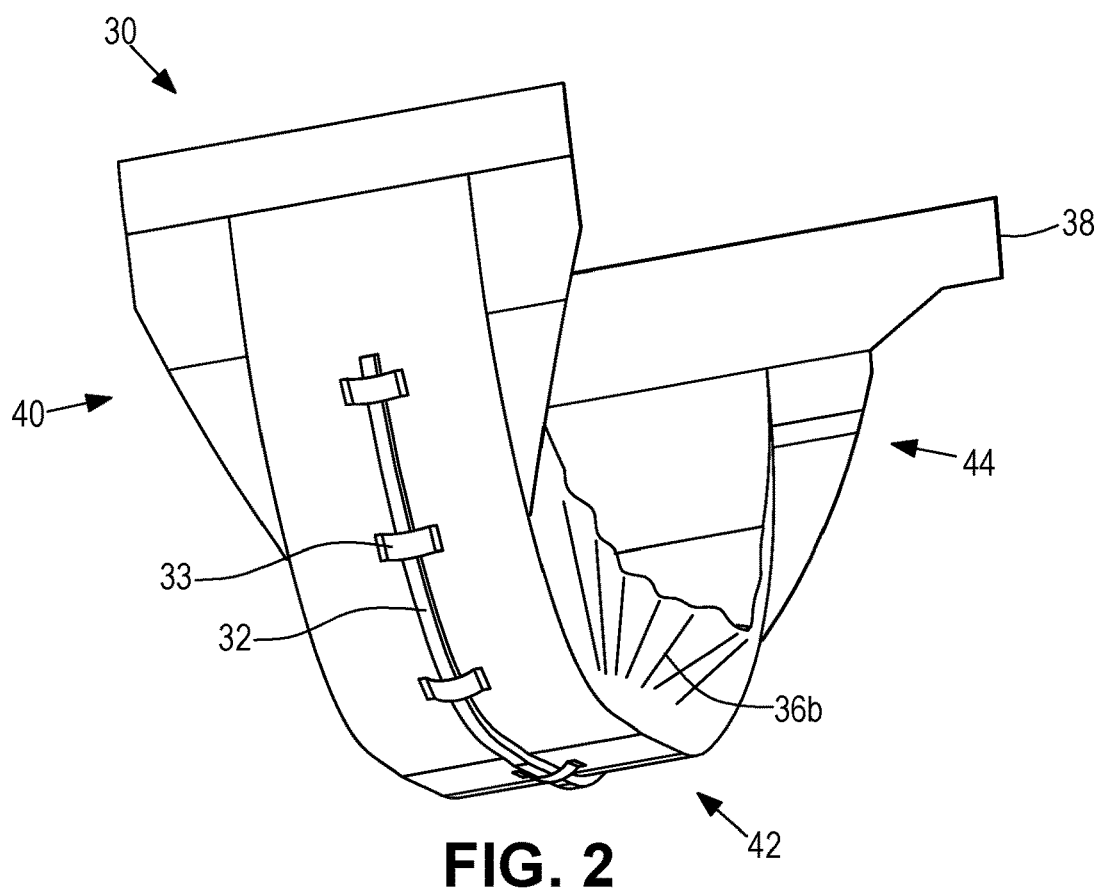
FIG. 2 shows a front bottom perspective view of the diaper of FIG. 1.

Referring now to FIG. 2 there is shown a front bottom perspective view of diaper 30, showing flexible band 32 extending until front area 40.

Figure 3:
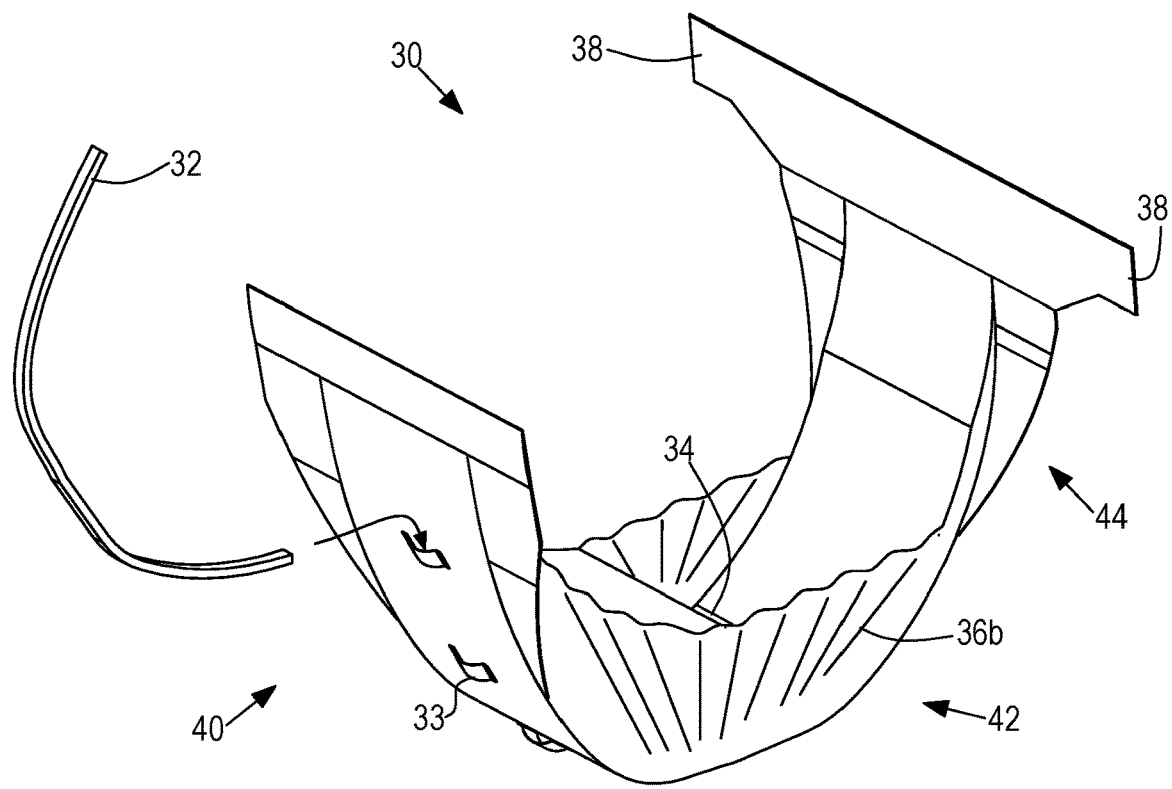
FIG. 3 shows a side perspective view of the diaper of FIG. 1 showing a flexible band being inserted into the diaper.

Referring now to FIG. 3 there is shown band 32 removed from diaper 30. If diaper 30 is made of cloth, it can then be washed for re-use. After diaper 30 is cleaned, band 32 may be inserted again.

If diaper 30 is disposable, it is discarded and band 32 may be inserted into a new diaper 30.

Figure 4:
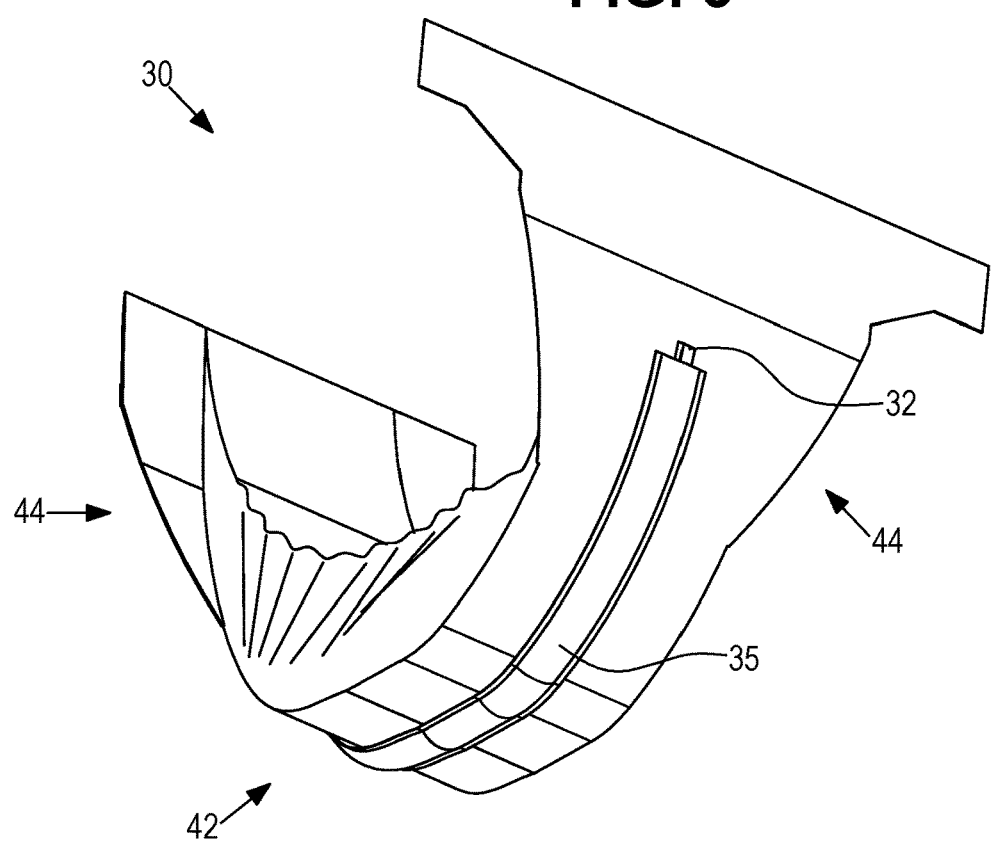
FIG. 4 shows the diaper having the flexible band disposed externally via a designated sleeve.

Referring now to FIG. 4 there is shown diaper 30 having flexible band 32 inserted into a designated sleeve 35 situated along the outer side of diaper 30. Sleeve 35 allows for flexible band 32 to be inserted into it and pulled out of according to need. Sleeve 35 positions flexible band 32 along the center of diaper 30 and maintains it there so that the movement of the wearer does not affect the position of flexible band 32, thus maintaining the shape of pocket 34.

Figure 5:
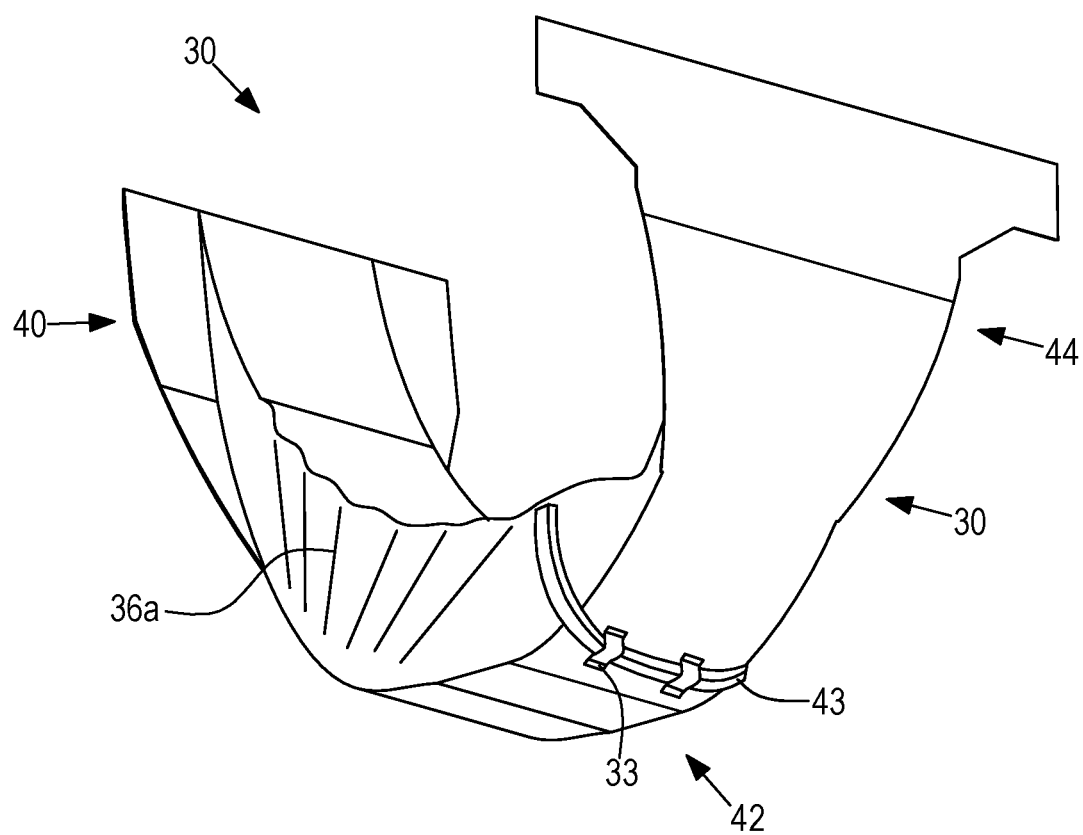
FIG. 5 shows the diaper having a transverse flexible band.

Referring now to FIG. 5 there is shown another embodiment of diaper 30 having a transverse flexible band 43, replacing flexible band 32, stretching from the end of cuff 36a to the end of cuff 36b. Transverse flexible band 43 defines a pocket 34 (see FIG. 3) formed in middle area 42.

Figure 6:
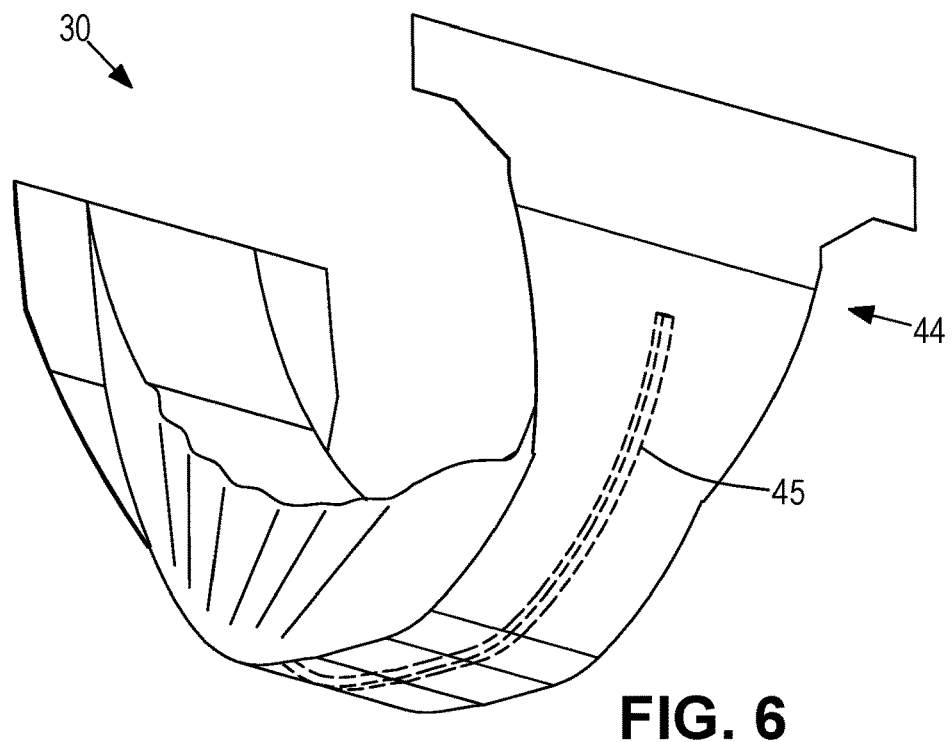
FIG. 6 shows a back bottom view of the diaper having the flexible band internally disposed.
Figure 7:
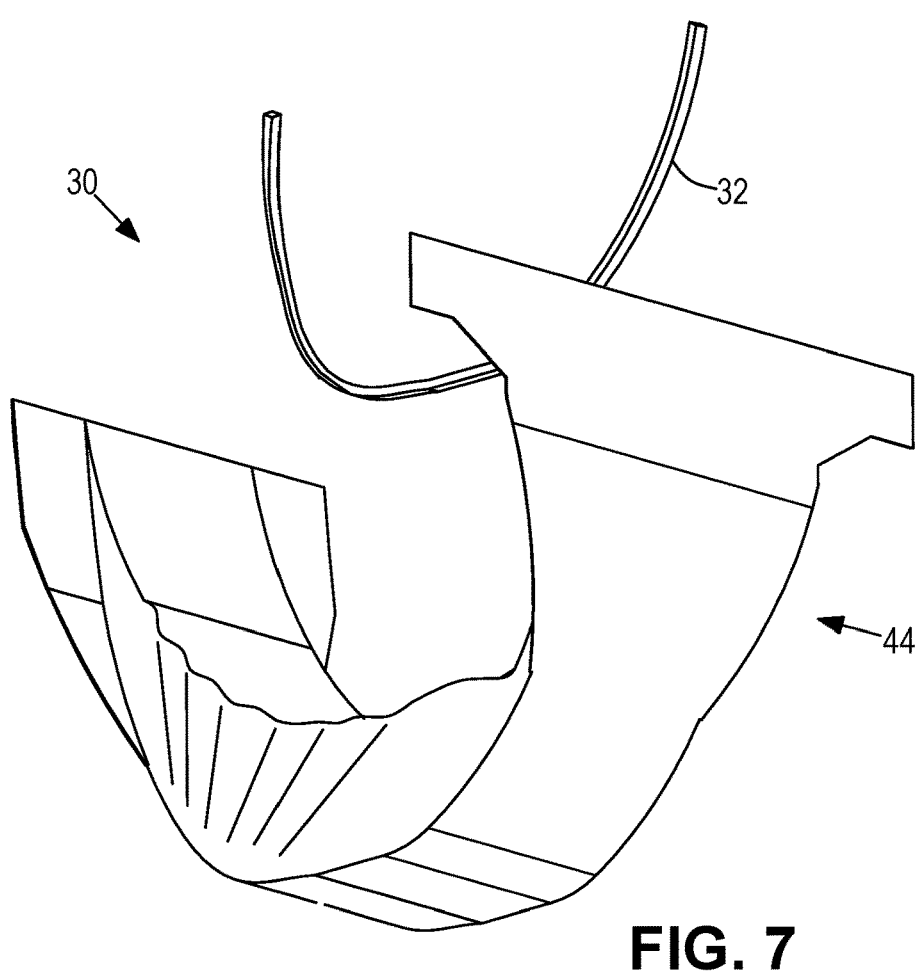
FIG. 7 shows the diaper of FIG. 5 showing the flexible band being inserted.

Referring now to FIGS. 6 and 7 there is shown diaper 30 having a designated internal sleeve 45 for inserting flexible band 32. Flexible band 32 is not visible once it is inserted into sleeve 45. Sleeve 45 positions flexible band 32 along the center of diaper 30 and maintains it there so that the movement of the wearer does not affect the position of flexible band 32, thus maintaining the shape of pocket 34. Flexible band 32 may be pulled out and released from internal sleeve 45, as shown in FIG. 7, when diaper 30 is soiled and needs to be washed in the case of a cloth diaper or discarded in the case of a disposable diaper. Flexible band 32 may be re-used and inserted into another diaper 30 having internal sleeve 45.

Figure 8:
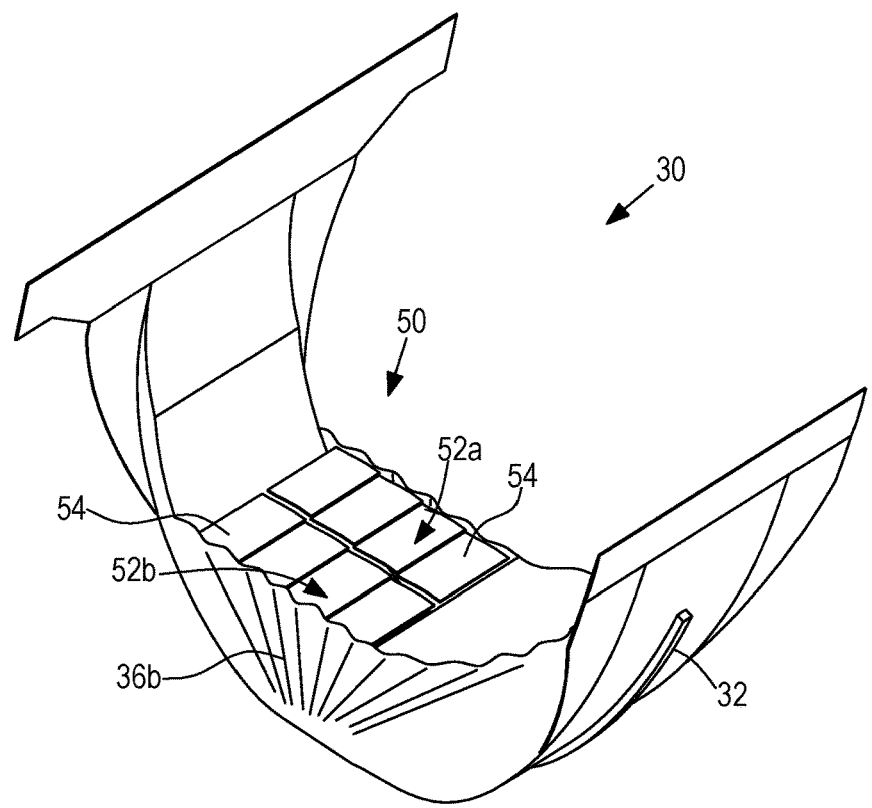
FIG. 8 shows a top perspective view of the diaper of FIG. 1 showing a one-way flexible partition.
Figure 9:
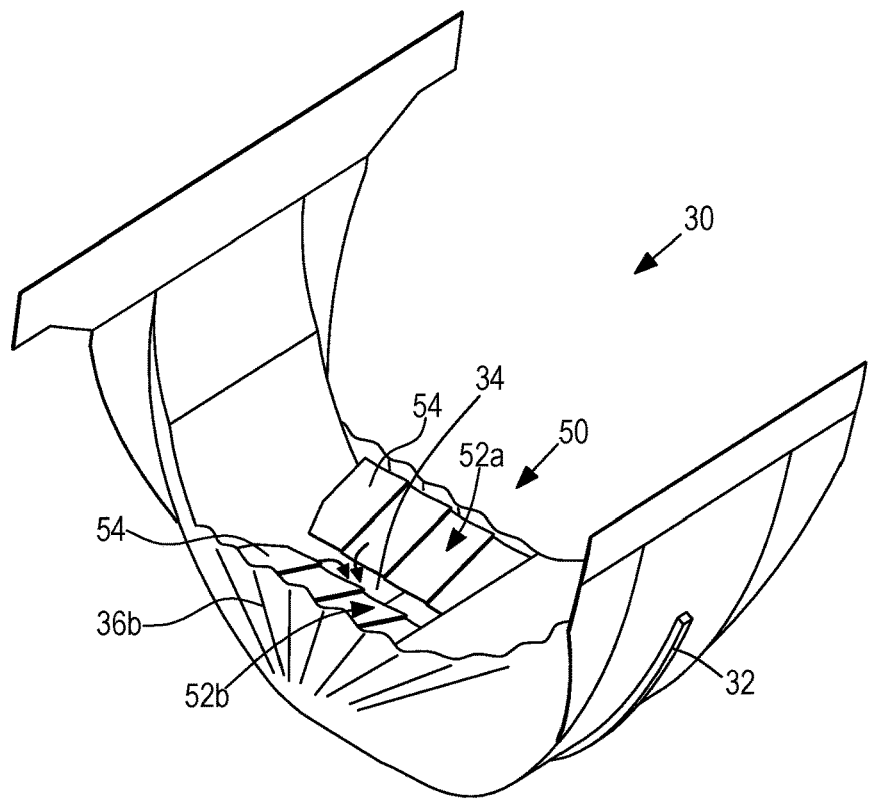
FIG. 9 shows the one-way flexible partition of FIG. 8, illustrating its movement towards the pocket.

Referring now to FIGS. 8 and 9 there is shown diaper 30 having flexible band 32 disposed on the outer side of diaper 30. A flexible partition 50 is provided to prevent the waste in pocket 34 from contacting the wearer's skin, thereby preventing skin irritation. The removable flexible partition 50 is made of a pair of dividers 52a and 52b, situated above pocket 34, each attached to leg cuff 36a and 36b, respectively. Each divider 52a-b is segmented into a plurality of flexible flaps 54 for preventing dividers 52a-b from resisting the weight of the waste. Flaps 54 are made of flexible material so that they are bent downwards to the direction of pocket 34, when solid waste is deposited in diaper 30. Flaps 54 are also made of smooth material so that the waste will slide off of them. Once the solid waste has passed through partition 50, flaps 54 return to their original position and serve as a cover over pocket 34 with the waste maintained in it.

Flexible partition 50 may be made of silicone, or any other material that is suitable for human use and that is flexible and smooth.

Partition 50 is removable, and is attached to leg cuffs 36a-b by Velcro™ or any other suitable means of attachment. Partition 50 may be removed from diaper 30 after being used, and then can be cleaned and re-attached to a clean diaper.

Partition 50 is illustrated herein extending in a transverse direction, although it may be extended in a longitudinal direction.

Figure 10:
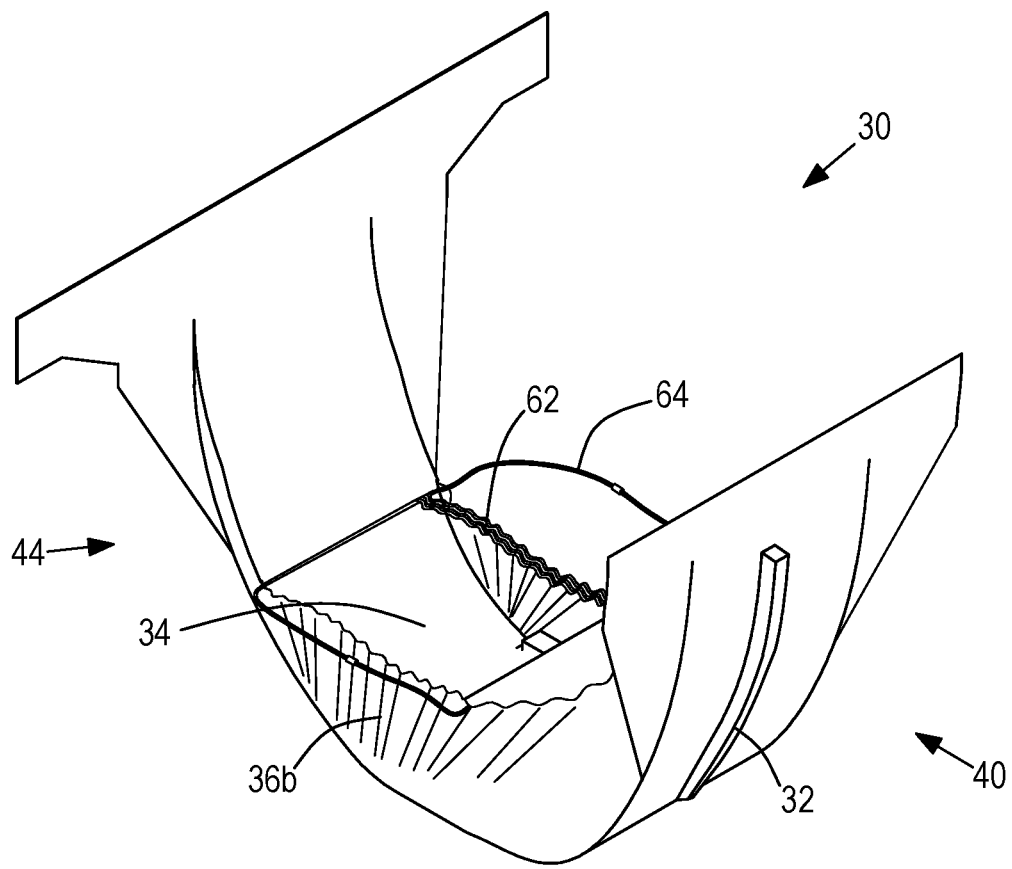
FIGS. 10-12 show another preferred embodiment of the diaper having a moveable cover sheet.
Figure 11:
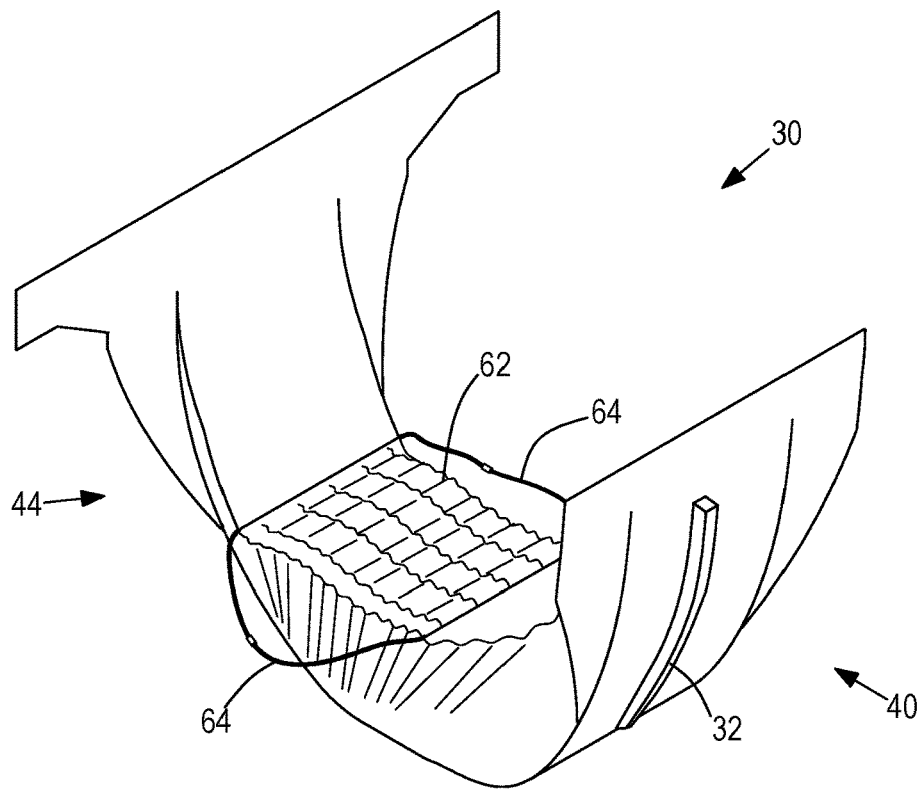
Figure 12:
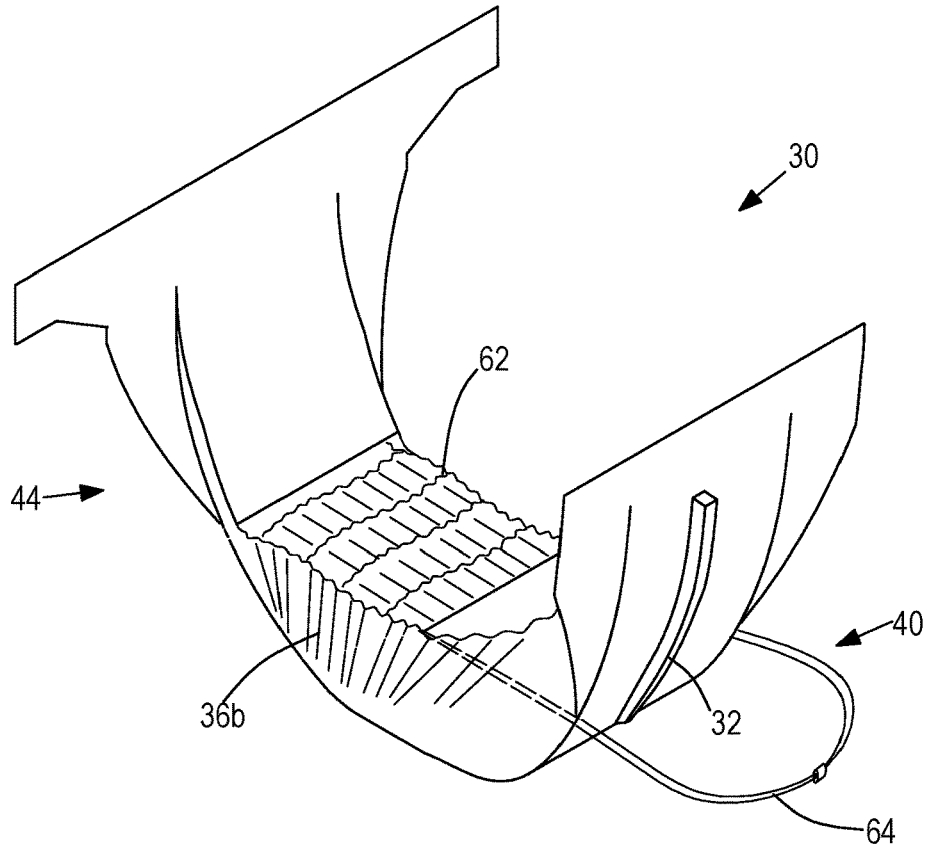

Referring now to FIGS. 10-12 there is shown an additional embodiment of the present invention showing diaper 30 provided with a cover 62 for pocket 34 area. Cover 62 is attached to string 64 and by pulling a portion of string 64 which is located externally to diaper 30, cover 62 is spread over pocket 34 (shown in FIG. 11) so that the solid waste contained in pocket 34 does not touch the skin. Cover 62 may be folded by pulling string 64 on the opposite side to expose pocket 34 in the case of re-use by the diaper 30 wearer. Cover 62 may be spread and folded as needed.

Cover 62 may be spread and folded from either direction, from the front 40 to the rear 44 of diaper 30, or as shown in FIG. 12 from cuff 36a to cuff 36b.

This feature is especially suitable for the elderly, who can open and close the cover themselves, more than once if needed, taking into consideration the diaper's 30 capacity limit.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

What is claimed is:

1. An anti-irritant diaper, comprising:
    an absorbent material constructed with a shape defined by a front area, a middle area, a rear area, a pair of leg cuffs and closing tabs;
    a resilient, flexible band removably disposed longitudinally and centrally along said absorbent material;
    a pocket formed within said middle area for receiving excreted solid waste, said pocket forming a space above it separating said pocket from the wearer's skin, said flexible band maintaining the structure of said pocket; and
    a removable one directional flexible partition comprising a pair of dividers situated above said pocket, each of said dividers being attached at one end to one of said pair of leg cuffs, each of said dividers being segmented into a plurality of flaps,
    wherein said flexible band maintains the structure of said pocket, such that said flexible partition allows for solid waste to enter therethrough and into said pocket, and said flexible partition returns to its position therefore preventing the waste from returning and then contacting the skin, thereby preventing irritation to the skin.

2. The anti-irritant diaper of claim 1 is made of cloth and can be re-used multiple times.

3. The anti-irritant diaper of claim 1 is disposable.

4. The resilient semi-rigid band of claim 1, wherein it is disposed externally to said diaper and is attached by a plurality of tabs disposed along said diaper.

5. The resilient semi-rigid band of claim 1, wherein it is inserted into said diaper via a dedicated sleeve formed in said diaper so that said band remains in place and for simplifying the insertion thereof.

6. The resilient semi-rigid band of claim 1, wherein said resilient flexible band is disposed internally to said diaper, via a designated sleeve formed in said diaper, said band being inserted into the absorbing material for the comfort of the wearer.

7. The resilient semi-rigid band of claim 1, wherein it may be removed and inserted into a new said anti-irritant diaper, multiple times.

8. The one directional flexible partition of claim 1, wherein said partition allows for excreted solid waste to pass therethrough into said pocket such that said flexible partition serves as a cover to said pocket so that the excreted solid waste does not touch the wearer's skin.

9. The removable one directional flexible partition of claim 1 wherein said partition may be removed, cleaned and then reattached to a clean diaper.

10. The anti-irritant diaper of claim 1, wherein the front area is thick for added absorbency.

11. An anti-irritant diaper, comprising:
    an absorbent material constructed with a shape defined by a front area, a middle area, a rear area, a pair of leg cuffs and closing tabs;
    a resilient, flexible band removably disposed longitudinally to said absorbent material;
    a pocket formed within said middle area for receiving excreted solid waste, said pocket forming a space above it separating said pocket from the wearer's skin, said flexible band maintaining the structure of said pocket; and
    a moveable top cover disposed above said pocket and attached to a pullable string, said string having a portion located externally to said diaper, and when said portion is pulled said top cover is spread over said pocket, wherein said flexible band maintains the structure of said pocket, such that solid waste enters said pocket and said top cover is spread over said pocket so that the waste is prevented from contacting the skin, thereby preventing irritation to the skin.

12. The moveable top cover of claim 11, wherein said pullable string may be pulled from an opposite direction whereby folding said top cover.

13. The moveable top cover of claim 11, wherein said pullable string may be pulled back and forth from said front area to said rear area of said diaper or from one said cuff to said second cuff.

14. An anti-irritant diaper, comprising:
an absorbent material constructed with a shape defined by a front area, a middle area, a rear area, a pair of leg cuffs and closing tabs;
a resilient, flexible band removably disposed transversely to said absorbent material;
a pocket formed within said middle area for receiving excreted solid waste, said pocket forming a space above it separating said pocket from the wearer's skin, said flexible band maintaining the structure of said pocket; and
a removable one-directional flexible partition comprising a pair of dividers being situated above said pocket, each of said dividers being attached at one end to one of said pair of leg cuffs, each of said dividers being segmented into a plurality of flaps,
wherein said flexible band maintains the structure of said pocket, such that said flexible partition allows for solid waste to enter therethrough and into said pocket and prevents the waste from returning and then contacting the skin, thereby preventing irritation to the skin.

* * * * *